United States Patent
Reesink et al.

(10) Patent No.: US 6,800,773 B2
(45) Date of Patent: Oct. 5, 2004

(54) CHEMICAL PROCESS

(75) Inventors: Bernard Hendrik Reesink, Doorn (NL); Marius Vaarkamp, Utrecht (NL)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 10/182,946

(22) PCT Filed: Feb. 5, 2001

(86) PCT No.: PCT/NL01/00088

§ 371 (c)(1),
(2), (4) Date: Nov. 25, 2002

(87) PCT Pub. No.: WO01/56692

PCT Pub. Date: Aug. 9, 2001

(65) Prior Publication Data

US 2003/0144537 A1 Jul. 31, 2003

(30) Foreign Application Priority Data

Feb. 3, 2000 (EP) .............................................. 00200371

(51) Int. Cl.$^7$ .............................................. C07C 51/36
(52) U.S. Cl. ...................................... 554/145; 554/141
(58) Field of Search ................................. 554/141, 145

(56) References Cited

U.S. PATENT DOCUMENTS

| 4,552,748 A | 11/1985 | Herrmann et al. |
| 6,005,143 A | 12/1999 | Parrillo et al. |

FOREIGN PATENT DOCUMENTS

| DE | 42 43 424 | 6/1994 |
| DE | 44 14 274 | 10/1995 |
| EP | 233642 | * 8/1987 |
| EP | 0 233 642 | 8/1987 |
| EP | 0 614 869 | 9/1994 |
| WO | WO 98 30323 | 7/1998 |
| WO | 98/30323 | * 7/1998 |

* cited by examiner

*Primary Examiner*—Deborah D. Carr
(74) *Attorney, Agent, or Firm*—Weingarten, Schurgin, Gagnebin & Lebovici LLP

(57) ABSTRACT

The invention is directed to a process for carrying out a chemical reaction in a reactor, comprising passing a reaction mixture in liquid phase through at least one structured reactor element present in said reactor, the internal surface of said reactor element that comes into contact with the reaction mixture being catalytically active, the improvement comprising passing said reaction mixture through the said at least one reactor element, said reaction mixture comprising at least one liquid and at least one gas in liquid phase.

30 Claims, 2 Drawing Sheets

Figure 1:
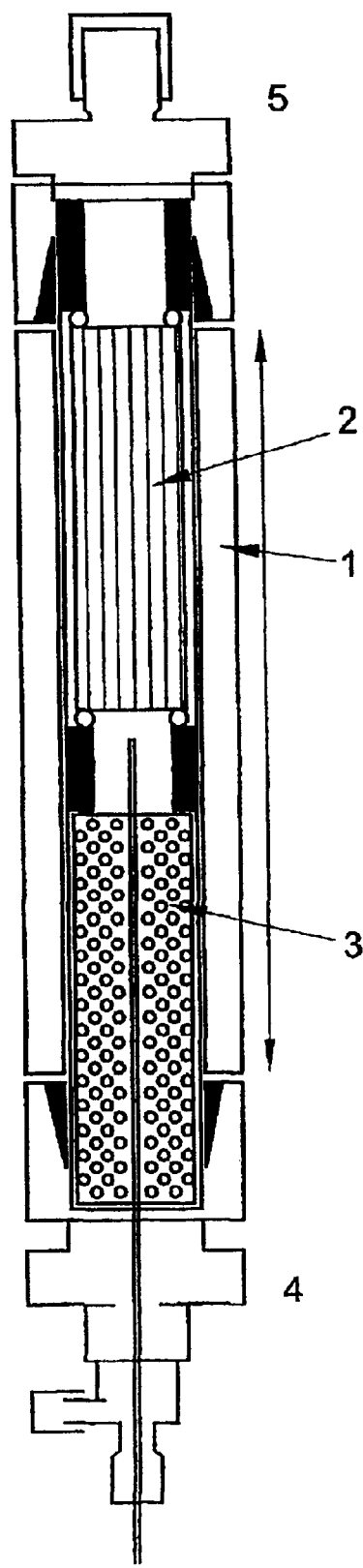

Run C561-01 : 2% tetraline/terpentina on C116-01 (~1% Pd-monolith)

27.274 a.u./% tetraline

| T(inlet) | runtime | reactor in | | | | reactor out | | | |
|---|---|---|---|---|---|---|---|---|---|
| | | UV | % arom. | % conv. | %arom/hr | UV | % arom. | Δ% arom. | % conv |
| 45 | 0 | 54.31 | 1.991 | 0.0 | | | | | |
| 50 | 30 | 53.54 | 1.963 | 1.4 | 0.056 | | | | |
| 50 | 60 | 53.06 | 1.945 | 2.3 | 0.036 | | | | |
| 80 | 90 | 51.84 | 1.901 | 4.6 | 0.089 | | | | |
| 88 | 120 | 46.54 | 1.706 | 14.3 | 0.388 | 40.76 | 1.494 | 0.212 | 12.4 |
| 89 | 180 | 33.15 | 1.215 | 39.0 | 0.491 | 26.39 | 0.968 | 0.248 | 20.4 |
| 89 | 240 | 17.38 | 0.637 | 68.0 | 0.578 | 12.73 | 0.467 | 0.171 | 26.8 |
| 89 | 300 | 3.38 | 0.124 | 93.8 | 0.513 | 1.764 | 0.065 | 0.059 | 47.9 |

- 650 ml average feed volume
- 28 ml effective monolith
- 1178 ml/hr feed throughput
- 42.1 LHSV
- 1.81 cycles/hr
- 0.55 residence time (hr)

CHEMICAL PROCESS

The invention is directed to a method of carrying out a chemical reaction, more in particular to a method for performing a chemical reaction between a liquid and a gas in liquid phase, catalysed by a heterogeneous catalyst. More in particular the present invention is relevant for the production of so-called 'fine chemicals', more complicated organic molecules, usually requiring multi-step production processes.

Heterogeneously catalysed chemical processes, especially those involving a liquid phase and a gas phase, such as hydrogenation reactions, suffer from the drawback that achieving good contact between the three phases (gas, liquid and solid) can be rather complicated. In order to get both a good activity and selectivity, the reactants in the gas and in the liquid phase should be thoroughly mixed. This creates restrictions on, among others, catalyst structure, yield, and reactor configuration.

Much effort has been put in understanding the phenomena that accompany these reactions. Up to now this has not resulted in a full understanding of what is going on.

One approach that has been taken in the research of the inventors to improve the contact between gas and liquid, is the use of monolith reactor systems. In these systems it is preferred to create so-called Taylor flow conditions in the reactor, thereby making sure that there is a sufficiently good distribution of gas and liquid. However, it has turned out to be difficult to arrive at a good understanding of the behaviour of the monolith system, thereby making it difficult to design the system in an optimal manner.

Another approach to solving the problems discussed above is described in WO-A 9601304. According to this document hydrogenation reactions are carried out in a solution of the substrate to be hydrogenated under supercritical or near-critical conditions. Disadvantages of this method are the high pressure and the additional supercritical solvent that are required and the necessity to recover the reaction mixture from the super- or near-critical phase, by pressure reduction. This makes such a process economically rather unattractive due to low concentrations of reactants coupled with high energy demands.

Accordingly it is an object of the invention to provide a process for carrying out a chemical reaction in a reactor, which process does not have the disadvantages described above.

The invention is directed to a process for carrying out a chemical reaction in a reactor, comprising passing a reaction mixture in liquid phase through at least one structured reactor element present in said reactor, the internal surface of said reactor element that comes into contact with the reaction mixture being catalytically active, the improvement comprising passing said reaction mixture through the said at least one reactor element, said reaction mixture comprising at least one liquid and at least one gas in liquid phase.

The term 'liquid phase' as used herein is intended to mean that the reaction components, gaseous reactant(s) and liquid reactant(s), form one liquid phase, substantially without gas phase. In other words the gas is dissolved in the liquid reactant, optionally also in the presence of solvent. Further this means that there is a true (subcritical) liquid phase and no supercritical fluid.

Surprisingly it has been found that by providing all reactants in the liquid phase to the catalytic structured reactor element in the reactor, the reaction is much better controlled, with higher activity and selectivity. Further the construction of the system can be made easier, thereby reducing capital costs.

Compared to the conventional slurry reactor, the system of the invention has the advantage that the filtration step in which the catalyst and the reactant mixture are separated from each other, is not needed.

Another advantage is that the hydrodynamics of the process are much simpler than for a process operated in a three phase monolith regime, i.e., the difficulties to satisfy conditions for Taylor flow are eliminated. Yet another advantage is that the short diffusion paths, typical for slurry phase reactions, are preserved in the structural reactor element, such as the monolith. The conventional alternative for this, a fixed bed reactor, typically has distinct disadvantages therein.

Finally, an advantage is that regardless of heat production or consumption of the reactions, the reactor can be more close to isothermal and the temperature may be controlled very accurately.

The invention is especially suitable for recirculating reaction mixtures, preferably with intermediate removal of reaction product(s) and suppletion of reactant gas. This makes it possible to control the composition of the reaction mixture very carefully. Wen using a large number of passes through the reactor or reactor element, conversion per pass through the reactor can be kept low, but the total conversion of the process can be very high, with high selectivity.

The use of a reactor containing at least one structured reactor element, allows the system to have very short contact times.

According to the invention the reactant mixture comprises at least one reactant that is liquid under the reaction conditions and at least one reactant that is gaseous under the reaction conditions, said at least one gaseous reactant being dissolved in the liquid system. By dissolving the gas, usually hydrogen, in the reactant mixture, it becomes possible to have high selectivity. In case of a once through system, the product is separated from the mixture. When using a recirculating system, such as a loop reactor, it is possible to have a relatively low conversion in each pass, with in total a high yield, due to the large number of passes. By multiple recirculation through the reactor it is thereby possible to obtain a high conversion (activity) combined with high selectivity. A loop reactor is defined herein as a reactor system, wherein part or all of the effluent is recycled to the reactor inlet. In the present case the reactor will contain at least one structured reactor element, either inside the loop or between reactor outlet and inlet.

Of special importance are the better performance of the reactor in general, more in particular compared to a slurry reactor, especially the higher activity and the absence of filtration.

Conversion per pass is of course limited by the amount of dissolved gas. This amount is determined by various process conditions, such as solubility of the gas in the reactant, temperature and pressure.

In general the present invention can be used for all reactions involving both gaseous and liquid components, including hydrogenation, oxidation, halogenation (chlorination), alkylation, acetylation, oxychlorination, hydro-dechlorination and the like. Gaseous components that may be used in relation to the present invention are hydrogen, oxygen, $N_2O$, $Cl_2$, ethylene, propylene, mixtures including these gases, and the like.

Preferably the system according to the invention is used for hydrogenation of organic compounds such as oleochemicals (fatty materials: fats and oils, fatty acids and derivatives such as fatty nitrils, alcohols and aldehydes), petroleum fractions such as distillates, resins and the like, nitro compounds, olefins, diolefins, aromatic compounds, and the like.

More in particular the invention can be applied very suitably to the production of fine chemicals, wherein it is of importance that high selectivity is maintained. Examples of reactions are hydrogenation, hydro-dechlorination, and the like.

In hydro-dechlorination the invention makes it possible to control the amount of hydrogen and the hydrogen/HCl partial pressures in the system very carefully, thereby substantially improving the selectivity of the reaction.

The process of the invention includes the use of a structured reactor element, such as a monolithic or honeycomb material, wherein the internal surface coming into contact with the reaction mixture is catalytically active. These reactor elements are well known, for example as exhaust gas catalyst (see for example Structured Catalysts and Reactors, A. Cybulski and J. A. Mouhijn (Eds), Marcel Dekker Inc., New York, 1998, pages 1–2).

Suitable monoliths to be used in the process of the invention have a structure defined as between 100 and 1500 cpi (channels per inch), preferably above 250 cpi.

In the operation of the present invention the surface of the reactor that is exposed to the liquid phase should be catalytically active. According to a first embodiment, this means that the reactor element contains catalytically active material applied thereto, for example on a washcoat of support material. This material is active for the intended reaction. Suitable materials for hydrogenation are the well known catalytic materials, such as nickel, cobalt, copper, manganese, precious metals, including platinum, ruthenium, rhodium palladium, iridium and the like; as well as combinations thereof. Likewise, for other reactions the catalyst can be oxides, mixed oxides, mixtures of metals and metal oxides, such as silica, alumina, silica-alumina, zeolites, clay minerals, combinations thereof, and the like.

The metal is applied in the conventional amounts for this type of catalyst, using washcoat, chemical vapour deposition, impregnation or other suitable techniques. It is also possible to use a reactor element having a surface that is active, or can be made active, for the specific reaction.

Impregnation may also suitably be used in a system where the reactor element is porous, has a washcoat or consists of a metal material that is treated to make the surface porous, followed by impregnation of the porous material.

In case of using a washcoat, the conventional amounts are used, such as between 0.5 and 5 g of washcoat per cubic inch of reactor element. A washcoat is a thin oxidic layer on a solid surface. The oxidic layer may itself be a catalyst, but it can also be converted into a catalyst by any method known to a person skilled in the art.

The invention is now further elucidated on the basis of a figure and examples, showing further embodiments and advantages of the invention.

In FIG. 1 a schematic representation of the test equipment is given, comprising a reactor 1, a monolith 2 of 2.0 by 15.2 cm as structured reactor element, a preheat section 3, consisting of 1 mm glassbeads and two semi circular 30 cm brass heating segments. The feed is introduced at 4 and the product is recovered from the reactor at 5.

A liquid reaction feed is saturated with a gas, prior to introduction at 4, in a unit, not shown. Optionally the reaction mixture from 5 can be returned to said unit, prior to feeding through 4.

Figure 2:
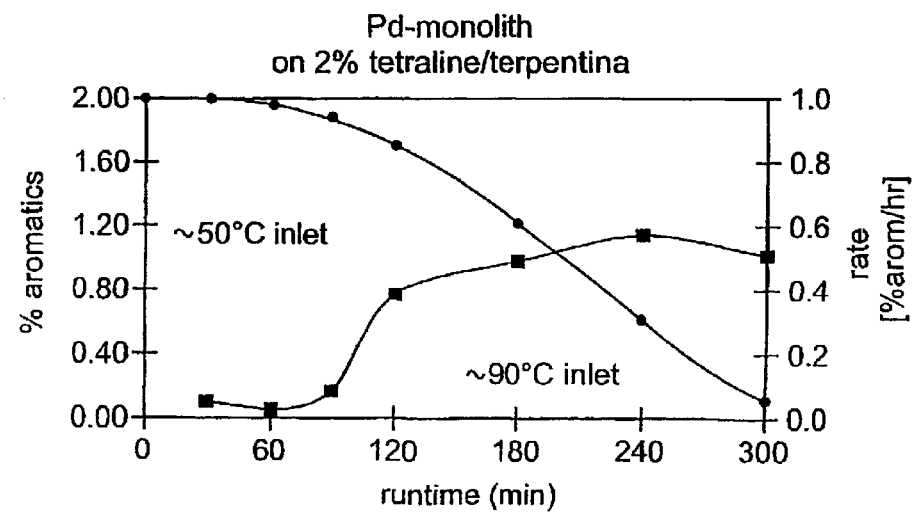

FIG. 2 gives in graphical form the results of the Example.

EXAMPLE 1

In the operation of the test, a 2 wt. % solution of tetraline in a mixture of alkanes as solvent, was saturated with hydrogen at 25 bar (abs) in an autoclave. After passing through a gas/liquid separator, the liquid phase was pressurised to 30 bar (abs) to ensure complete absence of gas phase.

The liquid was passed to the reactor of FIG. 1, after having been preheated to the reaction temperature. The results of the tests have been elucidated in the table and the attached graph (FIG. 2).

EXAMPLE 2

A solution of 1 wt. % 1-hexene in methanol was saturated with hydrogen at 5 bar. This solution was passed through a reactor as shown in FIG. 1 at 30° C. and 10 bar. The walls of the monolith were provided with an alumina washcoat, on which a homogeneous Rh-cyclooctadiene-1,2-bis-diphenylphosphini-ethane catalyst was tethered (attached) using a heteropolyacid.

A zero order hexene hydrogenation rate of 9 mmol $hr^{-1}$ was measured. Since only 0.078 mmol Rh was present this means a TOF of ~115 mol hexene per mol of metal per hour.

What is claimed is:

1. Process for carrying out a chemical reaction in a reactor, comprising passing a reaction mixture in liquid phase through at least one structured reactor element present in said reactor, the internal surface of said reactor element that comes into contact with the reaction mixture being catalytically active, the improvement comprising passing said reaction mixture through said at least one reactor element, said reaction mixture being without a gas phase present and comprising at least one liquid and at least one gas in liquid phase.

2. Process according to claim 1, wherein the said at least one reactor element comprises a monolith catalyst or a structured catalyst.

3. Process according to claim 2, wherein the reactant mixture comprises at least one reactant that is liquid under the reaction conditions and at least one reactant that is gaseous under the reaction conditions, said at least one gaseous reactant being dissolved in the liquid phase.

4. Process according to claim 1, wherein the reaction is a hydrogenation reaction.

5. Process according to claim 4, wherein the said hydrogenation reaction comprises the hydrogenation of a fatty material, the hydrogenation of a carboxylic acid, the hydrogenation of an aldehyde, the hydrogenation of aromatics and resins, the hydrogenation of olefins or diolefins, or the hydrogenation of a nitrite.

6. Process according to claim 1, wherein the catalytically active material is present on the inner walls of the monolith reactor.

7. Process according to claim 6, wherein the catalytically active material is present in the form of a washcoat.

8. Process according to claim 6, wherein the catalytically active material comprises a homogeneous catalyst, which is anchored on the inner surface of the monolith or the washcoat.

9. Process according to claim 1, wherein the monolith is present inside a loop reactor.

10. Process according to claim 1, wherein the reactant mixture is recirculated through the monolith at least twice.

11. Process according to claim 1, wherein the monolith reactor is based on a ceramic material, a metal or a metal alloy.

12. Process according to claim 2, wherein the reaction is a hydrogenation reaction.

13. Process according to claim 3, wherein the reaction is a hydrogenation reaction.

14. Process according to claim 2, wherein the catalytically active material is present on the inner walls of the monolith reactor.

15. Process according to claim 3, wherein the catalytically active material is present on the inner walls of the monolith reactor.

16. Process according to claim 4, wherein the catalytically active material is present on the inner walls of the monolith reactor.

17. Process according to claim 5, wherein the catalytically active material is present on the inner walls of the monolith reactor.

18. Process according to claim 7, wherein the catalytically active material comprises a homogeneous catalyst, which is anchored on the inner surface of the monolith or the washcoat.

19. Process according to claim 1, wherein:
at least one reactor element comprises a monolith catalyst or a structured catalyst;
the catalytically active material is present on the inner walls of the monolith reactor; and
the catalytically active material is present in the form of a washcoat.

20. Process according to claim 19, wherein the catalytically active material comprises a homogeneous catalyst, which is anchored on the inner surface of the monolith or the washcoat.

21. Process according to claim 2, wherein the monolith is present inside a loop reactor.

22. Process according to claim 2, wherein:
the catalytically active material is present on the inner walls of the monolith reactor; and
the monolith is present inside a loop reactor.

23. Process according to claim 2, wherein:
the catalytically active material is present on the inner walls of the monolith reactor;
the catalytically active material comprises a homogeneous catalyst, which is anchored on the inner surface of the monolith or the washcoat; and
the monolith is present inside a loop reactor.

24. Process according to claim 2, wherein:
at least one reactor element comprises a monolith catalyst or a structured catalyst;
the reactant mixture comprises at least one reactant that is liquid under the reaction conditions and at least one reactant that is gaseous under the reaction conditions, said at least one gaseous reactant being dissolved in the liquid phase;
the reaction is a hydrogenation reaction;
the said hydrogenation reaction comprises the hydrogenation of a fatty material, the hydrogenation of a carboxylic acid, the hydrogenation of an aldehyde, the hydrogenation of aromatics and resins, the hydrogenation of olefins or diolefins, or the hydrogenation of a nitrile;
the catalytically active material is present on the inner walls of the monolith reactor;
the catalytically active material is present in the form of a washcoat;
the catalytically active material comprises a homogeneous catalyst, which is anchored on the inner surface of the monolith or the washcoat; and
the monolith is present inside a loop reactor.

25. Process according to claim 2, wherein the reactant mixture is recirculated through the monolith at least twice.

26. Process according to claim 2, wherein:
the catalytically active material is present on the inner walls of the monolith reactor; and
the reactant mixture is recirculated through the monolith at least twice.

27. Process according to claim 24, wherein the reactant mixture is recirculated through the monolith at least twice.

28. Process according to claim 2, wherein the monolith reactor is based on a ceramic material, a metal or a metal alloy.

29. Process according to claim 2, wherein:
the catalytically active material is present on the inner walls of the monolith reactor; and
the monolith reactor is based on a ceramic material, a metal or a metal alloy.

30. Process according to claim 27, wherein the monolith reactor is based on a ceramic material, a metal or a metal alloy.

* * * * *